(12) United States Patent
Gupta et al.

(10) Patent No.: US 8,211,873 B2
(45) Date of Patent: Jul. 3, 2012

(54) ANTIAGING CHIRALLY-CORRECT MITOPROTECTANT AMINO ACID AND PEPTIDE COMPLEXES

(75) Inventors: Shyam K Gupta, Scottsdale, AZ (US); Linda Walker, Cardiff, CA (US)

(73) Assignee: Island Kinetics, inc., Chandler, AZ (US)

( * ) Notice: Subject to any disclaimer, the term of this patent is extended or adjusted under 35 U.S.C. 154(b) by 0 days.

(21) Appl. No.: 12/851,637

(22) Filed: Aug. 6, 2010

(65) Prior Publication Data

US 2010/0331274 A1 Dec. 30, 2010

Related U.S. Application Data (63) Continuation-in-part of application No. 12/485,302, filed on Jun. 16, 2009, now Pat. No. 7,834,210, and a continuation-in-part of application No. 11/308,290, filed on Mar. 15, 2006, now Pat. No. 7,569,558, and a continuation-in-part of application No. 10/604,999, filed on Aug. 29, 2003, now Pat. No. 7,320,797.

(51) Int. Cl.
  *C07C 229/36* (2006.01)
  *C07C 229/34* (2006.01)
  *A61K 8/02* (2006.01)
  *A61K 31/665* (2006.01)
  *A61K 31/315* (2006.01)
  *A61K 31/31* (2006.01)
  *A61K 31/30* (2006.01)
  *A61K 31/28* (2006.01)

(52) U.S. Cl. ........ 514/100; 424/400; 424/401; 562/440; 514/494; 514/497; 514/499; 514/505

(58) Field of Classification Search .................. 424/400, 424/401; 562/440; 514/494, 497, 499, 505
See application file for complete search history.

(56) References Cited

U.S. PATENT DOCUMENTS

| | | | |
|---|---|---|---|
| 5,952,373 A * | 9/1999 | Lanzendorfer et al. ....... | 514/456 |
| 7,666,442 B2 | 2/2010 | Morariu | |
| 2002/0173436 A1* | 11/2002 | Sonnenberg et al. ......... | 510/141 |
| 2005/0019354 A1 | 1/2005 | Perricone | |
| 2009/0281347 A1 | 11/2009 | Tachiya | |
| 2010/0151061 A1 | 6/2010 | Morariu | |

OTHER PUBLICATIONS

Berge et al., Pharmaceutical Salts, Jan. 1977, Journal of Pharmaceutical Sciences, vol. 66, No. 1, pp. 1-19.*
Bastin et al., Salt Selection and Optimisation Procedures for Pharmaceutical New Chemical Entities, 2000, Organic Proces Research and Development, vol. 4, No. 5, pp. 427-435.*

* cited by examiner

*Primary Examiner* — Johann R. Richter
*Assistant Examiner* — Luke Karpinski

(57) ABSTRACT

This invention relates to certain chirally-correct mitoprotectant phosphorylated heterocyclic agents [formula (I)], which are useful for the treatment of dermatological disorders that include challenged skin from cancer, diabetes, radiation treatments, chemotherapy, and sun-burn; mitochondrial dysfunction; age spots; acne, loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness; skin depigmentation, and combinations thereof;

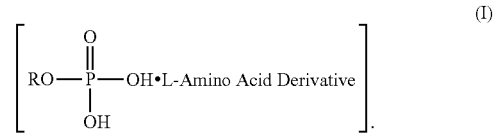

19 Claims, 3 Drawing Sheets

Table 1. Nomenclature of Chirally-Correct Amino Acid / Ester Complexes

Proposed INCI: L-Proline Benfotiamine

IUPAC: L-Proline -
S-[(2Z)-2-{[(4-amino-2-methylpyrimidin-5-yl)]methyl](formyl)amino}-5-(phosphono oxy)pent-2-ene-3-yl] benzenecarbothioate (1:1)

Proposed INCI: L-Proline Trehalose Phosphate

IUPAC::
L-Proline -
2-(phosphonooxymethyl)-6-[3,4,5,-trihydroxy-6-(hydroxymethyl)oxan-2-yl]oxy-oxane-3,4,5,-triol (1:1)

Proposed INCI: L-Proline-ATP

IUPAC:
L-Proline -
[(2R,3S,4R,5R)-5-(6-aminopurin-9-yl)-3,4,dihydroxyoxolan-2yl]methyl(hydroxyphosphonooxyphos phoryl)hydrogen phosphate (1:1) disodium salt FIG. 1. Nomenclature of Chirally-Correct Amino Acid / Ester Complexes.

FIG. 2. L-Tyrosine & Melanin Biosynthesis via Shikimate Pathway.

FIG. 3. Chiral Care for Challenged Skin.

ANTIAGING CHIRALLY-CORRECT MITOPROTECTANT AMINO ACID AND PEPTIDE COMPLEXES

The present invention is a continuation-in-part of U.S. patent application Ser. No. 10/604,999 (filed Aug. 29, 2003), now U.S. Pat. No. 7,320,797; U.S. patent application Ser. No. 11/308,290 (filed Mar. 15, 2006), now U.S. Pat. No. 7,569,558; and U.S. patent application Ser. No. 12/485,302 (filed Jun. 16, 2009) now U.S. Pat. No. 7,834,210.

BACKGROUND OF THE INVENTION

The enhancement of physical appearance occupies greater focus in human life than nearly all other daily life-related actions. There are far more consumer products available for the beautification of human body than for the treatment of human ailments. The improvement of skin tone and appearance is a growing, multibillion-dollar industry encompassing cosmetic, nutraceutical, pharmaceutical, and physical therapy disciplines. The consumer attention is focused on newest miracle ingredient in age-defying, anti-wrinkle, skin smoothing, skin brightening, and other similar antiaging agents, the newest prior art examples of which follow. Dumas et al (US 2010166814) disclose a cosmetic composition, which comprises a combination of at least two osmolytes chosen from the group comprising taurine or a derivative thereof, inositol, betaine and trehalose. This composition is intended for restoring, maintaining or reinforcing the moisturization of the skin and/or for protecting it against different types of stress and/or for preventing or retarding the appearance of the signs of aging of the skin, or for attenuating the effects thereof, or alternatively for promoting cell or tissue longevity. Yamamoto et al. (JP 2010018584) disclose a combination of poly-[gamma]-L-glutamic acid and/or its salt and an antiaging agent, which may be an anti-inflammatory agent and/or an antioxidant. Watanabe et al. (US 2009297645) disclose a skin antiaging agent comprising grape sap as an active ingredient, a method of preventing aging of skin using grape sap, and a method of using grape sap as a skin antiaging agent. Kang et al. (KR 20090078202) disclose a tripeptide to have regenerating effect of basement membrane, promote integrin generation and maintain proliferation ability; said tripeptide comprising Cu-GHK[Glycyl-L-histidyl-L-lysyl], GHK or AHK[L-alanyl-L-histidyl-L-lysine]. Woong et al. (KR20090078083) disclose a cosmetic composition containing adenosine and *Paeonia suffruticosa* extract to increase the synthesis of adenosine triphosphate and improve antiwrinkle effect. Walker (US 2008188424) discloses a series of compounds that are formulated using chirally correct ingredients, organic ingredients, and natural or naturally derived ingredients. Msika et al. (U.S. Pat. No. 7,638,149) disclose a novel peptide extract which has antimetalloprotease activity, in particular anticollagenase and antigelatinase activity. It also relates to the pharmaceutical, cosmetic or nutraceutical compositions comprising such an extract, in particular to a pharmaceutical composition intended to treat inflammatory diseases, such as arthrosis, parodontosis or ulcers, or to the cosmetic compositions intended to combat aging, which may or may not be actinic aging, or aging accelerated by tobacco and pollution. Sojka et al. (U.S. Pat. No. 7,306,809) disclose certain optically activated particles for use in cosmetic compositions. The optically activated particles diffuse ambient light and emit visible light to reduce the visual perception of imperfections including cellulite, wrinkles around the eyes and mouth, skin discoloration by veins and arteries, shadows, pores, mild scars, follicles, and blotchiness of the skin.

Every cell in the human body is packed with tiny organelles called mitochondria. Mitochondria are often referred to as "intracellular powerhouses" because they produce most of the energy used by the body. Cells with a high metabolic rate, such as heart muscle cells, may be equipped with thousands of mitochondria, while other cells may only contain a few dozen. The efficiency of mitochondrial energy production and function declines with age. Evidence is accumulating that mitochondrial dysfunction underlies many common age-related diseases, including skin aging, hair aging, Parkinson's disease, Alzheimer's disease, heart disease, fatigue syndromes, and numerous genetic conditions.

The present invention provides a comprehensive scientific solution to the problems associated with the biology of natural aging of skin or hair resulting from mitochondrial dysfunction.

SUMMARY OF THE INVENTION

The present invention discloses certain chirally-correct mitoprotectant phosphorylated heterocyclic agents [formula (I)], which are useful for the treatment of dermatological disorders that include challenged skin from cancer, diabetes, radiation treatments, chemotherapy, and sun-burn; mitochondrial dysfunction; age spots; acne, loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness; skin depigmentation, and combinations thereof. A topical delivery system for cellular energy support comprising the following is also disclosed: (i) a chirally-correct mitoprotectant agent, and (ii) an Intra-cellular antioxidant or free-radical neutralizing agent, and (iii) an anti-inflammatory agent, and (iv) a collagen or fibrin boosting agent. This delivery system encompasses support, repair, and protection against all the cellular mechanisms of glycation, MMP inhibition, DNA repair, osmoprotection, and heat and cold stress, among other key cellular mechanism that adversely impact mitochondrial functions.

The following terms used herein have the meanings set forth below.

Challenged Skin. Skin ailments caused by the diseases of the internal organs and their treatments. Examples include challenged skin condition from diabetes, cancer, radiation treatments, chemotherapy, and sun-burn (solar radiation).

Chirally-Correct. A molecule, complex, or ion-pair having a tetrahedral carbon atom with three different substituents, said carbon atom being a chiral carbon atom, and said chirality limited to L (or S) configuration.

d or l; (+) or (−). These signify the direction of the optical rotation of a molecule.

Hydrolyzed Protein. A protein that has been hydrolyzed to peptides or amino acids, or a combination thereof.

Ion-Pair. A compound formed by ionic bond between an electron donor and an electron acceptor agent, or a positively charged and a negatively charged agent.

D or L; R or S. Dextro (D) and Levo (L); Rectus (R) or Sinister (S) relate to right- or left-handed configuration of a chiral molecule or atom, respectively. These terms do not signify the direction of optical rotation of said chiral molecule.

L-Peptide. A peptide that contains L-amino acids or L-amino acids and glycine.

Mitochondrial Dysfunction. A loss or reduction of mitochondrial function resulting in a curtailment of cellular energy production.

Mitoprotectant. An agent that provides the protection of mitochondria from damage caused by natural or un-natural causes.

Organic. Being, containing, or relating to carbon compounds, especially in which hydrogen is attached to carbon whether derived from living organisms or not.

Osmoprotection. Protection of cellular function from the conditions of extreme dehydration.

Osmoprotective. Agents that provide osmoprotection.

Nomenclature. The nomenclature of representative examples, both according to the rules recommended by International Union of Pure and Applied Chemistry (IUPAC) and International Nomenclature of Cosmetic Ingredients (INCI) is presented in Table 1.

DETAILED DESCRIPTION

Mitochondrial energy production is an absolute necessity for physical strength, energy, stamina, and life itself. Even the slightest drop in mitochondrial energy output, no matter how subtle, can lead to weakness, fatigue and cognitive difficulties. Unfortunately, during aging, mitochondrial function—like just about everything else—becomes less efficient. A growing number of physicians and scientists believe that mitochondrial support nutrients may prove to be helpful for many of the symptoms associated with aging and age-related mitochondrial-induced diseases, including skin aging, Parkinson's disease, diabetes, and fatigue.

Mitochondrial energy production is accomplished by two closely linked metabolic processes: 1) the citric acid cycle (also known as the Krebs', or tricarboxylic acid cycle), and 2) oxidative phosphorylation. The citric acid cycle converts biological fuel (carbohydrates and fats) into adenosine-5'-triphosphate (ATP). ATP is the body's principal source of cellular energy.

The other process—oxidative phosphorylation—combines hydrogen with oxygen to generate even larger amounts of ATP. Oxidative phosphorylation generates about ten times more ATP than the citric acid cycle. Oxidative phosphorylation is the primary energy process for all aerobic organisms.

Mitochondrial oxidative phosphorylation provides over 80% of the ATP used by our cells for energy. Oxidative phosphorylation operates very efficiently—close to 70 percent. This compares with about 10% for internal combustion engines, and about 40% for hydrogen-oxygen fuel cells used in spacecraft.

Oxidative phosphorylation operates through the electron transport chain; a chain of five proteins embedded in the inner membrane of the mitochondria. These complexes include:
(i) NADH dehydrogenase,
(ii) Succinate dehydrogenase
(iii) Cytochrome-c reductase,
(iv) Cytochrome-c oxidase, and
(v) ATP synthase.

Oxidative phosphorylation converts adenosine diphosphate (ADP) to adenosine-5'-triphosphate (ATP)—the chemical energy "currency" of the cell—that can then be transported to where work needs to be done.

Age-Related Changes in Mitochondrial Function. The efficiency of mitochondrial energy production and function declines with age. Evidence is accumulating that mitochondrial dysfunction underlies many common age-related diseases, including skin aging, Parkinson's disease, Alzheimer's disease, heart disease, fatigue syndromes, and numerous genetic conditions.

Changes that occur with aging in mitochondria include (1) damage to mitochondrial DNA by free radicals; (2) decreased efficiency of the Krebs' cycle; (3) altered response to long term energy demands, (4) respiratory chain defect due to enzyme alterations; and (5) decreased membrane fluidity.

Mitochondria of healthy young adults respond differently to increased requirements for energy than older folks. Mitochondria of youthful people adapt to increased energy requirements by replicating rapidly. This results in more mitochondria producing more ATP for energy. However, as we age, our mitochondria replicate less readily. That means there are fewer mitochondria to produce the energy. These fewer mitochondria attempt to respond to increased demand by hypertrophying (increasing in size). Unfortunately these larger mitochondria are less efficient and produce more damaging free radicals than their more youthful, more numerous, and smaller progenitors.

These alterations in mitochondrial efficiency and function are at least partly related to alterations in concentration and efficiency of the elements of the respiratory chain. Most studies indicate a decrease in Complexes I (NADH dehydrogenase), II (succinate dehydrogenase), and IV (Cytochrome-c oxidase). In addition, as the amount of mitochondrial enzymes changes with age, the number of cells that totally lack cytochrome oxidase increases.

Free Radicals as a Cause of Mitochondrial Aging. Dr. Denham Harman first proposed mitochondrial dysfunction as an underlying cause of aging and age-related diseases in 1972. Following Harman's lead, other scientists modified or extended his theory. Dr. Jaime Miguel's Oxygen Stress-Mitochondrial Mutation Theory of Aging; Prof place in the respiratory chain where oxidative phosphorylation occurs. A team of researchers in the Department of Bio-chemistry and Biophysics at the University of Kalyani in India studied the effects of N-Acetyl Cysteine (NAC) on key elements of the respiratory chain. They administered NAC to mature (40 week-old) rats. After 20 weeks of treatment they found that the activities of Complex I, IV and V were significantly higher in the treated rats compared to the controls. NAC also helped to maintain levels of the important mitochondrial antioxidant, glutathione, as well as prevented cell death during in vitro studies. In other in vitro studies, NAC protected cells from "programmed cell death"—also known as apoptosis—by promoting oxidative phosphorylation, mitochondrial membrane integrity, and mitochondrial homeostasis.

Based on the science of skin biology, the following aspects are incorporated in the present invention to provide a comprehensive solution to treat the problems associated with natural skin aging resulting from mitochondrial dysfunction; (i) a phosphorylated mitoprotection agent, and a chirally correct cellular transport agent are chemically reacted, wherein said reaction results in the formation of a chirally correct mitoprotection agent, and wherein said mitoprotection agent may be additionally combined with (ii) an anti-inflammatory agent, and (iii) a collagen and/or fibrin boosting agent for comprehensive skin care via topical formulations.

Surprisingly and unexpectedly, the present invention discloses certain chirally correct phosphorylated heterocyclic mitoprotectant amino acid and peptide complexes, the generic structure of which is

Wherein said L-amino acid derivative is an L-amino acid, L-amino ester, or L-peptide, The complexes are conceptually related to U.S. patent application Ser. No. 11/308,290 (now U.S. Pat. No. 7,569,558), The chirally correct mitoprotectant amino acid and peptide complexes of the present invention are prepared in accordance to Chirally-Correct Complex Wherein;
R is selected from the group comprising, -continued Wherein,
Said L-amino acid is selected from the group comprising L-Alanine, L-Arginine, L-Asparagine, L-Aspartic acid, L-Cysteine, L-Glutamic acid, L-Glutamine, L-Histidine, L-Isoleucine, L-Leucine, L-Lysine, L-Methionine, L-Phenylalanine, L-Proline, L-hydroxyproline, L-Serine, L-Threonine, L-Tryptophan, L-Tyrosine, L-Valine, L-Hydroxyproline, and L-Pipecolic acid, and

Wherein,
Said L-amino ester is selected from the group comprising $C^1$-$C^{20}$ alkyl esters of L-Alanine, L-Arginine, L-Asparagine, L-Aspartic acid, L-Cysteine, L-Glutamic acid, L-Glutamine, L-Histidine, L-Isoleucine, L-Leucine, L-Lysine, L-Methionine, L-Phenylalanine, L-Proline, L-hydroxyproline, L-hydroxyproline, L-Serine, L-Threonine, L-Tryptophan, L-Tyrosine, L-Valine, L-Hydroxyproline, and L-Pipecolic acid, and Wherein, Said L-peptide is selected from the group comprising L-Carnosine, L-Glutathione, L-Anserine, L-dipeptide, L-tripeptide, L-tetrapeptide, L-pentapeptide, L-hexapeptide, hydrolyzed proteins, and combinations thereof.

The compounds of the present invention treat certain dermatological disorders that include challenged skin from cancer, diabetes, radiation treatments, chemotherapy, and sunburn; mitochondrial dysfunction; age spots; acne, loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness and combinations thereof. Additionally, certain benefits that appear contradictory to the above treatments, such as causing skin darkening, are also possible via concordant election of the compounds of the present invention for said treatments.

Cyclic amino acids, such as proline, hydroxyproline, and pipecolic acid have great importance in cellular biology. The distinctive cyclic structure of proline locks its φ backbone dihedral angle at approximately −75°, giving proline an exceptional conformational rigidity compared to other amino acids. Proline is commonly found as the first residue of an alpha helix and also in the edge strands of beta sheets. Proline is also commonly found in turns. Because proline lacks a hydrogen on the amide group, it cannot act as a hydrogen bond donor, only as a hydrogen bond acceptor. Multiple prolines and/or hydroxyprolines in a row can create a polyproline helix, the predominant secondary structure in collagen. The hydroxylation of proline by prolyl hydroxylase increases the conformational stability of collagen significantly. Hence, the hydroxylation of proline is a critical biochemical process for maintaining the connective tissue of higher organisms. Severe diseases such as scurvy can result from defects in this hydroxylation. For the above reasons, $R^1$ and $R^2$ can be a part of a five or six-member chirally-correct nitrogen heterocyclic ring, wherein said chirally-correct ion-pair complexes are prepared in accordance to

Wherein;

n=1, or 2, and

Figure 3:
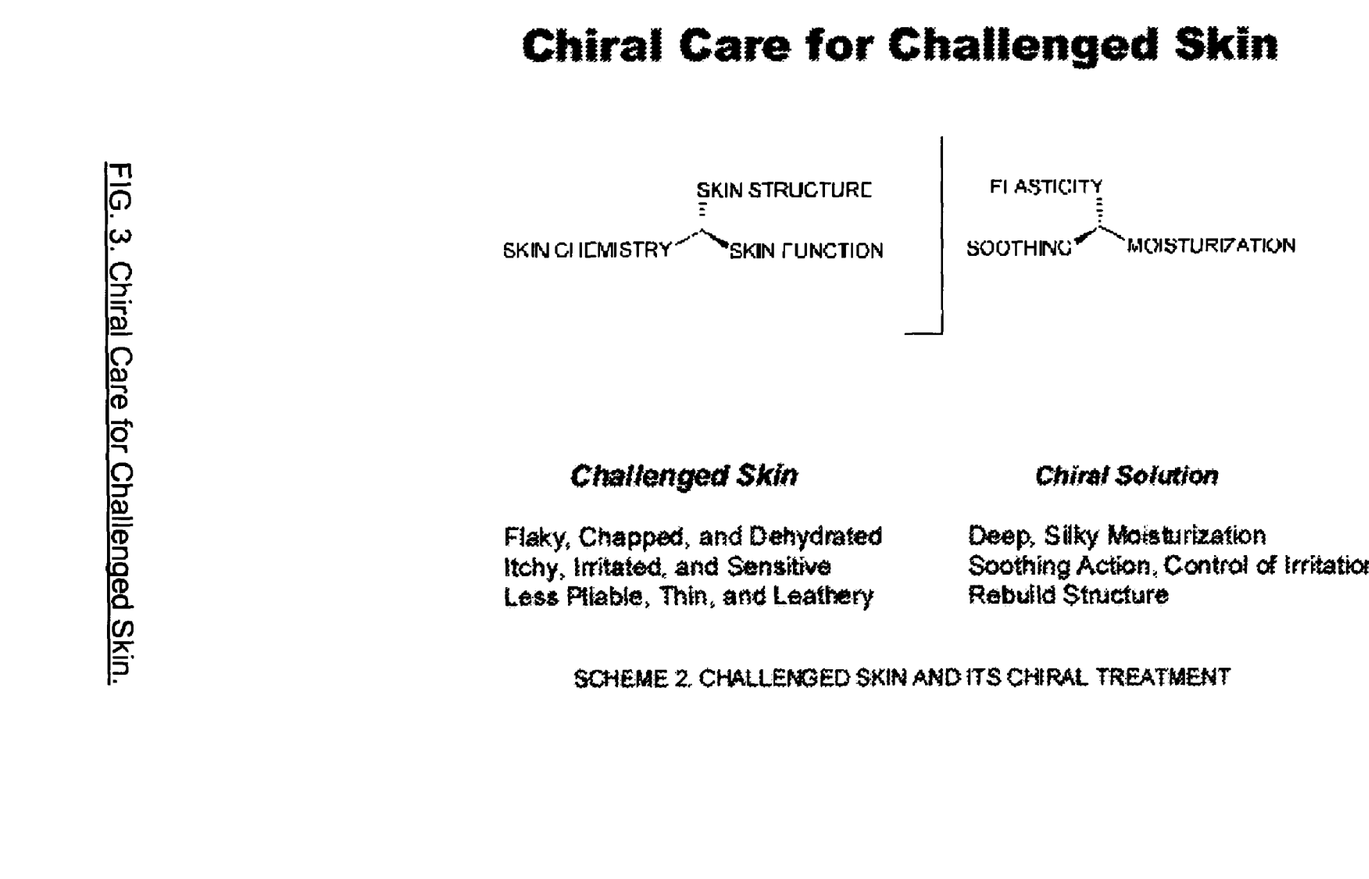
FIG. 3. Scheme 2. Challenged Skin and its Chiral Treatment.

R=as per FIG. 3, and $R^2$=H, or $C^1$-$C^{20}$ alkyl.

In addition to amino acids and their esters, peptides also provide complexes of the present invention. However, at least one of the amino acids in said peptide must have an L-configuration.

Skin penetration of peptides with higher molecular mass is now possible via the complexes of the present invention; argireline, a hexapeptide, can be made more bioavailable topically via its conversion into argireline-D-glucose-6-phosphate;

It is preferred to have the chirally correct mitoprotection agent incorporated in a suitable carrier base or a topical delivery system and any other desirable agents.

Prior art relevant to the present invention includes the use of a combination of benfotiamine and pyridoxamine (U.S. Pat. No. 7,666,442), neither of which—either alone or in combination—have any chirality, thus not related to the present invention. U.S. Patent Application Publication 20100151061 (Morariu) and 20050019354 (Perricone) similarly disclose compositions that do not contain the compounds of the present invention. JP1175939 discloses compositions that contain certain mixtures of ATP and amino acids, which are not the same as the compounds of the present invention. KR100844515 (Park) and EP2207569 (Bonke) disclose compositions that are not identical to the compounds of the present invention. Tachiya (US 20090281347) discloses preparation of certain amino acid phosphates from the reaction of an amino acid with phosphoric acid in the presence of an aromatic base such as pyridine. The presence of pyridine, a known carcinogen, is highly undesirable in any topical preparations such as the compositions and compounds of the present invention.

The compounds of the present invention are made by a chemical process wherein a chirally-correct agent is reacted with another agent that may or may not be chirally-correct, which comprises the combining of; (i) An organic phosphate agent, and (ii) An L-amino acid derivative, and (iii) A liquid reaction medium, and (iv) Heating at 50 to 120 degrees Celsius, and (iv) A pH of 3.0 to 6.5, if the reaction medium is aqueous. In the process of the present invention said liquid reaction medium is selected from the group consisting of water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methylpyrrolidone, pyrrolidone, and combinations thereof.

In the process of the present invention the formation of the compounds of the present invention is determined from the optical rotation data at several wavelengths. Optical rotation data for L-Proline Benfotiamine (Sample A061610D in A) and L-Proline-D-glucose-6-phosphate are presented in Table 2. For example, when L-Proline Benfotiamine (A061610D in col. A) is synthesized from benfotiamine and L-proline (Col. B) the optical rotation data, as determined by an outside testing laboratory (col. E) are quite different than the same values calculated on the basis of simple additivity of optical rotation of individual components (col. F). Similarly, for L-proline-D-glucose-6-phosphate (C062110B, col. A) synthesized from L-proline and D-glucose-6-phosphate (col. B) the optical rotation data, as determined by an outside testing laboratory (col. E) are quite different than the same values calculated on the basis of simple additivity of optical rotation of individual components (col. F). These data are further detailed in Table 2.

TABLE 2

OPTICAL ROTATION DATA.

| Sample (A) | Composition, gm (B) | Appearance (C) | Wavelength (D) | Optical Rotation (Actual) (E) | Optical Rotation (Calculated) (F) |
|---|---|---|---|---|---|
| A061610D L-Proline Benfotiamine | Benfotiamine 1.0 L-Proline 4.0 Water 150.0 | Solution | 589 nm 546 nm 436 nm 405 nm 365 nm 325 nm | −2.9 −3.2 −5.4 −6.4 −8.1 −0.3 | −7.5 −5.1 −2.8 −4.8 −5.7 −2.4 |
| JS071010E Benfotiamine | Benfotiamine 1.0 Water 154.0 | Suspension (Benfotiamine is insoluble in water) | 546 nm 436 nm 405 nm 365 nm 589 nm 325 nm | Not readable due to insolubility | |
| A071410A L-Proline | L-Proline 4.0 Water 151.0 | Solution | 589 nm 546 nm 436 nm 405 nm 365 nm 325 nm | −7.5 −5.1 −2.8 −4.8 −5.7 −2.4 | |
| A061010C L-Proline | L-Proline 1.11 Water 98.89 | Solution | 589 nm 546 nm 436 nm 405 nm 365 nm 325 nm | −1.0 −1.1 −1.9 −2.3 −3.0 −1.9 | |
| C062110B L-Proline-D-glucose-6-phosphate | D-Glucose-6-phosphate 2.82 L-Proline 1.11 Water 96.07 | Solution | 589 nm 546 nm 436 nm 405 nm 365 nm 325 nm | −0.0 −0.0 −0.1 −0.1 −0.1 −0.1 | +1.8 +0.8 −0.8 −0.5 −0.8 −1.0 |
| C071310B D-Glucose-6-phosphate | D-Glucose-6-phosphate 2.82 Water 97.17 | Solution | 589 nm 546 nm 436 nm 405 nm 365 nm 325 nm | +2.8 +1.8 +1.1 +1.8 +2.2 +0.9 | |

The role of antioxidants and free radical neutralizing agents in reducing skin aging process and skin wrinkle reduction is well known in the prior art. The antioxidants and free radical neutralizers can be included in the present invention for the protection of skin at the deeper skin renewal layers where fresh skin cells are generated. For this reason, an intracellular antioxidant or free radical neutralizer can also be beneficial. Among the antioxidants with multiple functions that are useful in combination with the agents of the present invention include Abyssine, Cloudberry, Acai, Acetyl L-Cysteine, Acetyl L-Carnitine, L-Adenine, Adenosine, Aldavine, Aldenine, Alfalfa, Allantoin, Arbutin, Ambiaty, Ameliox, Arctic Cranberry, Arganyl, Artemisia, L-Ascorbic Acid, Ascorbyl Palmitate, Asiatic Acid, Astaxanthin, Beta Carotene, Betulinic Acid Extract, Bilberry, Blueberry Extract, Camu Camu, Canadian Willowherb, Catalase, Cat's Claw, Chemmoya, Cranberry, Emblica, Gallic Acid, Giant Knotweed, Goji Berry, Green Tea Extract, Guava Extract, Heather Extract, Kakadu Plum, Kiwi Extract, Kudzu Zymbiozome Fermentum, Litchiderm, Lycopene, Magnesium Ascorbyl Phosphate, Magnolia Extract, Mangosteen, Marshmallow Extract, Melitane, Milk Thistle, MitoProtect (Nanoheart), Natrulon, Nectapure, Noni Extract, Peumus Boldus Leaf Extract, Phycocyanin, Phytic Acid, Plantaga, *Pueraria Mirifica*, Pumpkin Extract, Quercetin, Red Clover, Red Wine Extract, Resveratrol, Retinyl Palmitate, Rhodiola, Rooibos Tea, Superoxide Dismutase, Tetrahydrocurcuminoids, Thioredoxin, Thioctic Acid, Thiotaine, Thyme Extract, Tocopherol, Tocopherol, Turmeric Extract, Ubiquinone, Venuceane, White Peony Extract, White Tea Extract, and combinations thereof.

Anti-inflammatory agents can be included in the present invention to reduce the skin irritation caused by environmental, personal hygiene, body beautification, and dietary/personal habits situations. Skin irritation is known to cause the degradation of collagen, which results in skin wrinkles. The examples of environmental conditions that can cause skin irritation include dry air, UV, sunlight, free radicals, air pollutants, and such. The examples of personal hygiene conditions that can cause skin irritation include use of soap and cleansers, shaving and hair removal agents, and such. The examples of body beautification that can cause skin irritation include fragrances, cosmetics, and other body decorative agents. The examples of dietary/personal habits conditions that can cause skin irritation include the use of foods rich in fats that can enhance prostaglandin synthesis in the body, excessive use of tobacco, and alcohol, all of which are known to cause skin irritation.

Most anti-inflammatory agents function by decreasing prostaglandin production through their inhibition of cyclooxygenase-1 (COX-1), cyclooxygenase-2 (COX-2), and lipoxygenase-5 (LOX-5) enzymes. The uses of massage or vasodilator ingredients for the removal of lactic acid from areas of inflammation are well known therapies. The initiation of inflammation by reactive oxygen species (such as superoxide anions) has been recognized. Recently, the role of Substance P in neurotransmission of pain from inflammatory response has been recognized. The inhibition of inflammatory cytokines in the development of new anti-inflammatory therapies is actively being studied. In addition, excessive nitric oxide (NO) production by activated macrophages has recently been implicated in several inflammatory diseases including arthritis. These aspects have been described in further detail in U.S. Pat. Nos. 5,494,668; 5,888,514; 5,854,291; and 5,916,565.

Collagen and fibrin boosting agents can also be included in the present invention. It is well known that with natural aging process the production of collagen and fibrin slows down. This causes skin thinning, loss of skin elasticity, and formation of wrinkles. The inclusion of collagen or fibrin boosting agents in any comprehensive antiaging treatment is thus of biological importance for skin regeneration.

It is well recognized in the scientific community that delivery systems are highly useful in cosmetics and pharmaceutical disciplines. In a recent article written by one of the present inventors (Cosmetic Delivery Systems, Household & Personal Products Industry, commonly known as HAPPI magazine, January 2003 issue, page 79) the definition and benefits of a number of prior art delivery systems have been discussed. A delivery system is thus a combination of both art and science that can improve the performance and consumer appeal of a consumer product or composition.

The present invention also discloses a topical delivery system comprising scientific combination of chirally correct mitoprotectant amino acid/ester and peptide complexes for healthy skin biology and a high-performance delivery system to provide a comprehensive solution to the problems associated with skin disorder. Said method of topical delivery for cellular energy support comprising mixing of, (i) a mitoprotectant compound of claim 1, and (ii) an antioxidant agent, and (iii) an anti-inflammatory agent, and (iv) a collagen-boosting agent with a carrier, and wherein said mixture is applied to skin.

Quaternary ammonium compounds have been commonly used in modern skin care agents for various benefits that include conditioning, shine, skin smoothing, and such. These ammonium compounds, which are cationic in nature, also contain an anionic counter-ion as an ion-pair. For example, Crodasorb UV-HPP (Polyquaternium-59) is a polymeric quaternary ammonium composition in which chloride and methosulfate are attached as anionic counter-ions. It is well appreciated by those who are versed in this art that only the cationic part of such quaternary ammonium agents provides skin care benefits such as preventing damage by UV, and protection of tensile strength, hydrophobicity, and protection of skin's natural color. In another example, Incroquat UV-283 (Cinnamidopropyltrimonium chloride), a UV-absorbing quaternary ammonium compound, provides protection from damage by UV and free radicals. In this example, the cationic Cinnamidopropyltrimonium moiety of this composition provides such benefits, and the anionic (chloride) part does not provide any skin beneficial effects. In the chirally correct mitoprotectant amino acid and peptide ion-pair complexes of the present invention both anionic and cationic moieties of said complexes provide cellular benefits to both dysfunctional mitochondria, and the folding of DNA.

The importance of intra-cellular antioxidants in antiaging agents has received spotlight in recent years. The incorporation of botanical antioxidants in cosmetic products is gaining popularity due to anti aging and other skin tone enhancement benefits, concordant to their use as nutritional supplements. Cosmetic products formulated with familiar antioxidants (vitamin E, Coenzyme Q10, ascorbic acid, lipoic acid, and soy isoflavones, etc.) have appeared in the marketplace with promissory claims. The design of a topical antioxidant product offers challenges: A wide spectrum antioxidant product should control intra-cellular oxidation resulting from biochemical mechanisms including oxygen, free radicals, UV, atmospheric pollutants, oxidative enzymes, catabolic oxidation, and chemical oxidation. The selection of functional intra-cellular antioxidants and free radical neutralizers to control complex, frequently inter-related biochemical oxidation mechanisms, and design of topical delivery systems to assure bioavailability via absorption through skin are of paramount importance.

A combination of antioxidants is more effective than a single antioxidant on an equal weight basis due to antioxidant cascade mechanism. It is well known that antioxidants belong to various chemical classes, such as polyphenols, carotenoids, flavonoids, and such. Some examples follow. (Chemical class is indicated in parentheses.) Rutin (flavone), Quercetin (flavone), Hesperidin (flavone), Diosmin (flavone), Mangiferin (xanthone), Mangostin (xanthone), Cyanidin (carotenoid), Astaxanthin (carotenoid), Xanthophyll (carotenoid), Lycopene (carotenoid), carotene (carotenoid), resveratrol, (polyphenol), tetrahydrocurcumin (polyphenol), rosmarinic acid (polyphenol), ellagic acid (polyphenol), hypericin (polyphenol), chlorogenic acid (polyphenol), oleuropein (polyphenol), lipoic acid (disulfide), glutathione-oxidized (disulfide), cystine (disulfide), N-acetyl-cystine (disulfide), glutathione-reduced (sulfhydryl), cystein (sulfhydryl), and N-acetyl-cysteine (sulfhydryl).

The present invention proposes that a combination of antioxidant ingredients should be included from different chemical classes to control intra-cellular oxidation resulting from various biochemical mechanisms. Most of these antioxidants also possess anti-inflammatory and antimicrobial properties. The total quantity of antioxidants should be balanced carefully, as an excessive amount of antioxidants may have an opposite, pro-oxidant effect resulting in poor stability and performance of the product. The use of antioxidant synergists offers additional advantages. The key function of such synergist is to reconvert the antioxidant free radical into its original non-radical state followed by its self-destruction into neutral, harmless molecules. Hydroxy acids (citric, ascorbic, tartaric, etc.), frequently used for this purpose. Coenzyme Q10, vitamin C, and quercetin have also been reported as synergists.

A great variety of collagen and fibrin boosting ingredients have now become commercially available that are also known to assist in the cellular functions. Such ingredients are also be included in the compositions of the present invention, the examples of which include *Withania Somnifera* Root Extract, *Ascophyllum Nodosum* Extract, *Asparagopsis Armata* Extract, *Veronica Appendiculata* Leaf Extract, *Betula Alba* (Birch) Bark/Leaf Extract, *Silybum Marianum* Fruit Extract, Aminoguanidine HCL, *Malus Domestica* Fruit Cell Culture, *Argania Spinosa* Leaf Extract, Acetyl Hexapeptide-8, *Vaccinium Myrtillus* (Bilberry) Extract, *Rubus Fructicosus* (Blackberry) Fruit Extract, *Borago Officinalis* Seed Oil, *Buddleja Davidii* Meristem Cell Culture, Tetrahexyldecyl Ascorbate, Carnosine (L), Catalase, *Centella Asiatica* Meristem Cell Culture, Caprooyl Tetrapeptide-3, Mixed Mucopolysacchardies, Glycogen, Tripeptide-2, *Leontopodium Alpinum* Meristem Cell Culture, *Phyllanthus Emblica* Fruit Extract, *Acmella Oleracea* Extract, Vitex Agnus Castus Extract, Ascorbyl Tetraisopalmitate, Palmitoyl Hexapeptide-6, Lycium Barbarum Extract (Goji Berry), *Macrocystis Pyrifera* Extract, *Saccharomyces*/Xylinum Black Tea Ferment, Pentapeptide-3, Soy Isoflavones, *Theobroma Cacao* (Cocoa) Seed Extract, *Camellia Sinensis* Leaf Extract, *Garcinia Mangostana* Peel Extract, *Litchi Chinesis* Pericarp Extract, *Machilus Bark Extract*, Mallotus Bark Extract, Glycosaminoglycans, Citrus *Aurantium Duclis* (Neroli) Flower Oil, sH-Polypeptide-15, Simmondsia Chinensis (Jojoba) Seed Oil, *Opuntia Ficus* Fruit Extract, *Pisum Sativum* (Pea Peptide) Extract, Acetyl Octapeptide-3, Dipeptide Diaminobutyroyl Benzylamide Diacetate, Palmitoyl Dipeptide-5, Palmitoyl Dipeptide-6, Thioctic (R-lipoic) Acid, L-Ergothioneine, Acetyl Tetrapetide-2, and Glycerin Soja (Soybean) Protein.

Anti-inflammatory agents are required in the present invention to reduce the skin irritation caused by environmental, personal hygiene, body beautification, and dietary/personal habits situations. It is to be noted that a mixture of two or more anti-inflammatory agents, especially those that belong to different biochemical mechanism classes, is more beneficial than corresponding equal weight amounts of a single ingredient. This is due to various different biochemical mechanisms by which such anti-inflammatory agents provide their beneficial effect. A number of both synthetic and natural agents have thus become available; some of such examples follow (the biochemical mechanisms of their action are indicated in the parentheses). Ginger Root, or *Zingiber Officinale* Root Extract (COX-2 inhibitor), Galanga, or *Alpinia Officinarum* Extract (LOX-5 inhibitor), Turmeric, or *Curcuma Longa* Root Extract (Superoxide inhibitor), Mango Ginger, or *Curcuma amada* (Unknown mechanism), tetuin, *Capsicum*, or *Capsicum Annuum* Extract (Substance P inhibitor, Vasodilation, Superoxide inhibitor), Clove Family, or *Syzygium Aromaticum* Extract (COX-1, COX-2 inhibitor), *Evodia*, or *Evodia Rutaecarpa* Fruit Extract, (COX-2 inhibitor), *Boswellia*, or *Boswellia Serrata* Extract (LOX-5 inhibitor), SAMe, or S-Adenosylmethionine (Catecholamine metabolism), Eucomis, or Eucomis L"Herit (COX-1 inhibitor), Celastrus, or *Celastrus orbiculatus* (COX-1 inhibitor), Tithonia, or *Tithonia diversifolia* (Cytokine inhibitor), Kochia, or *Kochia Scoparia* Extract (COX-2 inhibitor), *Scoparia*, or *Scoparia dulcis* Extract (Analgesic), Qiang Huo, or *Notopterygium incisum* (COX-1, LOX-5 inhibitor), Cinnamon, or *Cinnamonum cassia* (Nitric oxide scavenger), Mexican Bamboo, or *Polygonum cuspidatum* (Nitric Oxide scavenger), Ogon, *Baikal Scullcap*, or *Scutellaria baicalensis* (COX-2 inhibitor), Coptis, Xianglian, or Coptis chinenesis (Nitric oxide inhibitor), Psoralea, Rumex, *Baccharis*, Feverfew, *Vitis, Stephania* (unknown mechanisms), and *Corydalis*, or *Corydalis Turtschaminovii* Root Extract (Analgesic).

Ginger has been in use in Ayurvedic and Tibetan medicine for centuries. Ginger extracts are known to increase peripheral blood flow with a feeling of warming and tingling sensation. Ginger contains essential oils and spicy substances such as gingerol, shogaol, zingerone, and capsaicin; those spicy substances are principally responsible for its pain relieving properties. Recent scientific studies suggest that inhibiting the COX-2 enzyme may be an effective way to reduce inflammation without the side effects associated with irreversible COX-1 inhibition. Ginger inhibits COX-2, and also 5-lipoxygenase (LOX-5) enzyme.

Turmeric (*Curcuma longa*) rhizomes contain curcumin and its derivatives (curcuminoids) that are bright yellow in color. Their hydrogenated derivatives, tetrahydrocurcuminoids, are nearly colorless materials. All of these ingredients possess excellent anti-inflammatory activity. Tetrahydrocurcuminoids offer advantages in topical cosmetic applications due to their lack of color. The steam distillation of turmeric rhizomes provides turmeric oil, reported to possess excellent anti-inflammatory activity.

Galanga (*Alpinia officinarum*), also known as Galangal or Chinese Ginger, is native to China, Thailand, and India. It contains essential oils, gingerols, and a group of pungent substances, diarylheptanoids. The studies have shown diarylheptanoids (and analogous phenyl alkyl ketones) to possess excellent anti-arthritic properties due to their arrest of prostaglandin biosynthesis via inhibition of 5-lipoxygenase. *Capsicum*, Capsaicin: The ancient Maya folk-healers used cayenne pepper (*Capsicum frutescence*) for the treatment of toothache and general body pain. In modern Western medicine, capsaicin has been used to treat pain associated with neuralgia, neuropathy, osteoarthritis, rheumatoid arthritis, bladder pain, and stomach pain. Capsaicin is the active analgesic ingredient present in *capsicum* preparations. It is a topical analgesic that may inhibit the synthesis, transport, and release of substance P, a neurotransmitter of pain. Capsaicin is also a vasodilator.

Clove Family. Clove oil and clove buds have been in use for the treatment of toothache and muscular pains since ancient times. A number of plants in this family, notably *Syzygium aromaticum, Syzygium corynocarpum,* and *Syzygium mallacense*, are known to contain pain-relieving constituents. Eugenol, a vasorelaxant and analgesic constituent of *Syzygium aromaticum*, also possesses strong anti-inflammatory activity. The extracts of *Syzygium corynocarpum* and *Syzygium malaccense* inhibit prostaglandin biosynthesis via blocking of COX-1 and COX-2 enzymes. The extract from the bark of *Syzygium cumini* has been shown to possess excellent anti-inflammatory activity without any gastric side effects. Acetyl eugenol, a component of clove oil, has recently been shown to alter arachidonic acid metabolism, resulting in reduced formation of thromboxane.

*Evodia*: This herb has been used for dysentery in Chinese medicine (Wu Zhu Yu) since ancient times. Rutaecarpine, obtained from *Evodia rutaecarpa*, is a new class of recently introduced anti-inflammatory ingredients that directly inhibits COX-2 enzyme. Antinociceptive and anti-inflammatory activities of the extracts of this plant have recently been reported. Evodiamine, and its analogs present in *Evodia rutaecarpa* also possess vasodilatory and analgesic activity.

Frankincense, *Boswellia*: Guggal (*Boswellia serrata*) has been used for the treatment of arthritis in Ayurvedic medicine for centuries. Frankincense, myrrh, and gold were among three presents brought by the Wise Men to the infant Christ. It is interesting that all three of these have been used in the treatment of gout and arthritis in ancient history of medicine. *Boswellia* is currently one of the most popular alternative medicines for inflammation. Recent research has identified three key ingredients (grouped as boswellic acids) that are responsible for the anti-inflammatory action of *Boswellia serrata* extracts. Recent research has firmly established that Boswellic acids and their derivatives are specific inhibitors of leukotriene synthesis by their direct interaction with 5-lipoxygenase.

SAMe (S-Adenosylmethionine): It has received wide interest for the treatment of osteoarthritis since its discovery in 1952. This substance, present in all living organisms, is required for over 40 biochemical functions in human body. It has been proven to enhance the formation of cartilage, and provide pain relieving anti-inflammatory action.

*Eucomis*: South African traditional medicine has extensively utilized the extracts of bulb, leaves, and root of this plant for pain, inflammation, and fever. Recent work has shown that the extracts from bulb have the highest level of COX-1 inhibitory activity.

*Celastrus*: This oriental folk medicine has been used for rheumatoid arthritis. Recent work has identified strong COX-1 activity ascribed to epiafzelechin, a member of flavan-3-ols, present in this herb. Tithonia: The extracts of Tithonia are used in Central America for the treatment of haematomas. Recent work has shown the constituents of this extract, diversifolin and tirotundin, to possess anti-inflammatory activity. Interestingly, the anti-inflammatory activity was from the inhibition of the synthesis of inflammatory mediators such as cytokines and chemokines.

*Scoparia*: The herb *Scoparia dulcis* is used in Brazilian folk medicine to treat bronchitis, gastric disorders, hemorrhoids, insect bites and skin wounds, and in oriental medicine to treat hypertension. Recent studies have shown that extracts of *Scoparia dulcis* have analgesic, anti-inflammatory, and sympathomimetic activity.

Qiang Huo: The root extracts of this Chinese medicinal herb traditionally used for arthritis and joint pain have recently been shown to possess COX-1 and LOX-5 inhibitory activity.

Cinnamon: The traditional use of cinnamon as a vasodilator for pain and inflammation in the Middle Eastern and other countries has long been practiced. Recent disclosures have confirmed the anti-nociceptive and anti-inflammatory activity of cinnamon extract via its direct scavenging of nitric oxide and peroxynitrite.

*Polygonum*: This herb is more commonly known as Mexican Bamboo (Mexico) and Hu Zhang (China). Various species of *Polygonum* have recently been identified to contain anti-inflammatory constituents that modulate the production of NO by activated macrophages. Recent results suggest that *Polygonum tinctorium* extract may be a potential therapeutic modulator of NO synthesis in various pathological conditions.

Ogon (Ougon): *Scutellaria*, used in Japanese Kampo herbal medicine (Ogon), China, (Sanhuang), and in Baikal region of Russia, has shown anti-inflammatory, anti-hepatitis, antibacterial, antiviral, anti-tumor, and anti-oxidant activity. The anti-inflammatory activity is ascribed to its active components, baicalin, baicalein and wogonin. In a recent study, wogonin tested as a direct inhibitor of COX-2, NO-production, and prostaglandin production, indicating its potential use in the treatment of topical inflammatory diseases. Baicalin, in another study, showed chemokine inhibiting activity. Baikalein has shown LOX-5 inhibiting activity.

Coptis: Coptis, a Chinese herbal medicine (Xianglian) also used in Japan, is well known for its antibacterial properties due to its high berberine content. It also contains several lignans (isolariciresinol, lariciresinol glycoside, pinoresinol, pinoresinol glycoside, and syringaresinol glycoside) with anti-inflammatory properties. Woorenosides, isolated from Coptis japonica, have shown anti-inflammatory activity via their inhibition of NO production.

*Psoralea glandulosa*: An ancient Persian medicine, *Psoralea glandulosa* contains bakuchiol, cyclobakuchiols, and angelicin that possess anti-pyretic and anti-inflammatory activity. *Psoralea corylifolia*, an Ayurvedic medicine in India (Babchi) and BuGuZhi in China, possesses anti-inflammatory, anti-pyretic, and analgesic activity due to its bavachinin content. Bakuchiol, recently isolated from the same plant, inhibits NO synthase gene, with implications for its anti-inflammatory activity.

*Rumex patientia* (Dock) has shown anti-inflammatory activity.

*Baccharis*: Several species of *Baccharis* have shown analgesic and anti-inflammatory activity, principally due their inhibition of prostaglandin biosynthesis.

Feverfew: This phytopharmaceutical (*Tanacetum parthenium*) is well known for its fever and migraine alleviation benefits. Recently, its anti-nociceptive and anti-inflammatory activities, due to its LOX-5 and COX inhibition, have been reported *Vitis*: The grape family is well known for its potent antioxidant constituents, especially procyanidins and resveratrol. Recently, tetramers of resveratrol found in *Vitis amurensis*, have been found to possess strong anti-inflammatory activity via their inhibition of leukotriene biosynthesis. This is not surprising, as several antioxidants are also known to possess anti-inflammatory activity: This property may be due to their inhibitory effect on LOX and COX enzymes.

*Stephania*: *Stephania* has long been used in Korea as an analgesic and anti-inflammatory agent for joint swelling. Tetrandrine, an alkaloid found in *Stephania japonica* is well known for its anti-inflammatory activity. Cepharanthine, an alkaloid found in *Stephania cepharantha*, has revealed vasodilatory effects with enhanced microcirculation.

*Tinospora*: Ayurvedic and Islamic practitioners in India have used *Tinospora cardifolia* for liver jaundice, various skin diseases, rheumatism, fever, and syphilis. Clinical studies conducted with human arthritis have demonstrated its anti-inflammatory properties. The inhibition of nitric oxide synthesis appears to be a factor for this activity.

Additional examples of anti-inflammatory agents include Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (Vitis-Vinifera) leaves, apigenin, phytosan, and luteolin.

Collagen and fibrin boosting agents are also required in the present invention. It is well known that with natural aging process the production of collagen and fibrin slows down. This causes skin thinning, loss of skin elasticity, and formation of wrinkles. The inclusion of collagen or fibrin boosting agents is thus of biological importance for skin regeneration. The collagen or fibrin boosting composition can be selected from, but not limited to, glucosamine, N-acetyl-glucosamine, chondroitin, algae extracts, chitosan, niacinamide, niacinamide derivatives, copper nucleotides, zinc nucleotides, manganese nucleotides, glutathione, carnosine, vitamin C, vitamin E, vitamin A, Coenzyme Q10, lipoic acid, dimethylamino ethanol, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), copper nucleotide, zinc nucleotide, manganese nucleotide, copper glucoside, zinc glucoside, manganese glucoside, and combinations thereof.

Since living parts of hair and nail are also very similar to skin in aging process, the agents of the present invention are also useful for hair and nail antiaging agents.

EXAMPLES

The following examples are presented to illustrate presently preferred practice thereof. As illustrations they are not intended to limit the scope of the invention. All quantities are in weight %.

Example 1

Preparation of L-Proline Benfotiamine Complex

Procedure: Prepare a 0.1 molar solution of L-proline in distilled water. Also prepare a 0.1 molar solution of benfotiamine in warm 1:1 water/ethanol. Mix equal amounts of the two solutions, heat at 45 to 55 C until optical rotation stabilizes. L-Proline Benfotiamine Complex thus produced is used directly in compositions comprising this compound. The structure of this compound is shown, Example 2

Alternate Preparation of L-Proline Benfotiamine Complex

Procedure: L-proline (4.0 gm), benfotiamine (1.0 gm) and water (150 gm) are mixed and heated at 45 to 55 C until a clear solution of L-Proline Benfotiamine Complex thus produced is obtained. It is used directly in compositions comprising this compound. The optical rotation data at various wavelengths are included in Table 2.

Example 3

Preparation of L-Proline Trehalose Phosphate Complex

Figure 1:
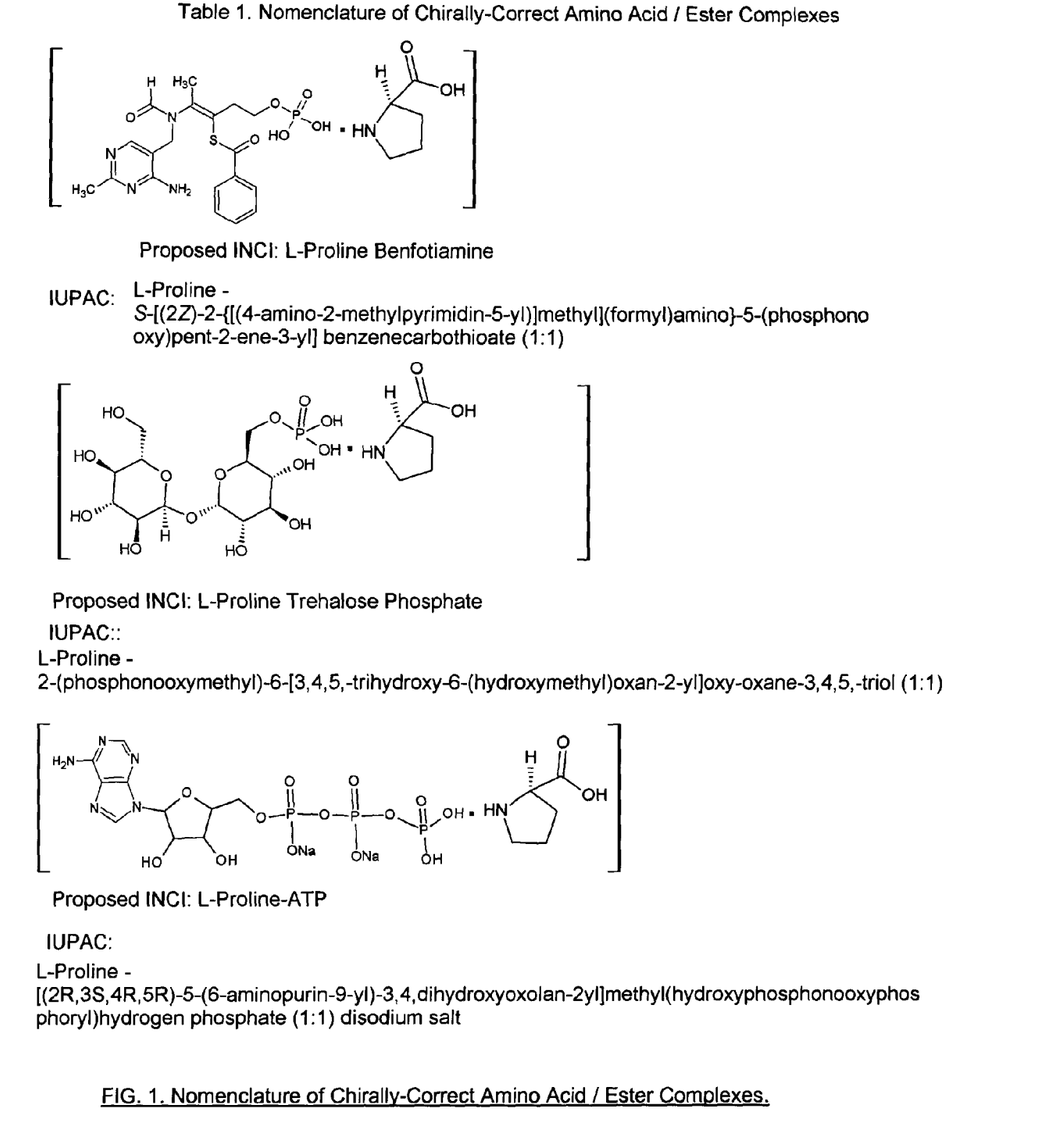
FIG. 1. Table 1. Nomenclature of Chirally-Correct Amino Acid/Ester Complexes.

Procedure: Prepare a 0.1 molar solution of L-proline in distilled water. Also prepare a 0.1 molar solution of trehalose phosphate in warm water. Mix equal amounts of the two solutions, heat at 45 to 55 C until optical rotation stabilizes. L-Proline Trehalose Phosphate Complex thus produced is used directly in compositions comprising this compound. The structure of this compound is illustrated in FIG. 1.

Example 4

Preparation of L-Proline-D-Glucose-6-Phosphate

Procedure: L-proline (1.1 gm), D-glucose-6-phosphate (2.82 gm) and water (96.07 gm) are mixed and heated at 45 to 55 C until a clear solution of L-Proline-D-glucose-6-phosphate thus produced is obtained. It is used directly in compositions comprising this compound. The optical rotation data at various wavelengths are included in Table 2. The structure of this compound is shown,

Example 5

Preparation of L-Proline Disodium ATP Complex

Procedure: Prepare a 0.1 molar solution of L-proline in distilled water. Also prepare a 0.1 molar solution of disodium adenosine-5'-triphosphate in warm water. Mix equal amounts of the two solutions, heat at 45 to 55 C until optical rotation stabilizes. L-Proline Adenosine-5'-triphosphate Complex thus produced is used directly in compositions comprising this compound. The structure of this compound is illustrated in FIG. 1.

Example 6

Preparation of L-Carnosine-D-Glucose-6-Phosphate Complex

Procedure: Prepare a 0.1 molar solution of L-carnosine in distilled water. Also prepare a 0.1 molar solution of D-Glucose-6-Phosphate in warm water. Mix equal amounts of the two solutions, heat at 45 to 55 C until optical rotation stabilizes. L-Carnosine-D-Glucose-6-Phosphate complex thus produced is used directly in compositions comprising this compound. The structure of this compound is illustrated,

Example 7

Preparation of L-Tyrosine-D-Glucose-6-Phosphate Complex

Procedure: Prepare a 0.1 molar solution of L-tyrosine in distilled water. Also prepare a 0.1 molar solution of D-Glucose-6-Phosphate in warm water. Mix equal amounts of the two solutions, heat at 45 to 55 C until optical rotation stabilizes. L-Tyrosine-D-Glucose-6-Phosphate complex thus produced is used directly in compositions comprising this compound. The structure of this compound is illustrated,

Example 8

Skin Darkening and Anti-Wrinkle Serum

Ingredients. (1) Ethyl Lactate 20.0 (2) Polyalkyleneoxy Polyamide 0.5 (3) L-Tyrosine-D-glucose-6-phosphate 1.0 (4) PEG-6 78.0 (5) Preservatives 0.5. Procedure. Make serum base by mixing (1) to (3) at room temperature or slight heating. Pre-mix (4) to (6) to a clear solution and add to main batch with mixing. The product has light green serum like appearance.

Example 9

Anti-Acne Cream

Ingredients. (1) Deionized water 82.0 (2) Cetearyl alcohol (and) dicetyl phosphate (and) Ceteth-10 phosphate 5.0 (3) Cetyl alcohol 2.0 (4) Glyceryl stearate (and) PEG-100 stearate 4.0 (5) Ethyl Lactate 5.0 (6) Glutathione-D-glucose-6-phosphate 0.5 (7) Zinc salicylate 1.0 (8) Preservatives 0.5. Procedure. Mix 1 to 5 and heat to 75-80° C. Adjust pH to 4.0 4.5. Cool to 35-40 C with mixing. Add 6 to 8 with mixing. Adjust pH to 4.0-4.5, if necessary. An off-white cream is obtained.

Example 10

Skin Discoloration and Age Spots Cream

Ingredients. (1) Water 55.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Water 5.0 (15) Niacinamide Lactate 1.0 (16) Niacinamide Hydroxycitrate 3.1 (17) Glutathione-d-glucose-6-phosphate 0.5 (18) Paeonol 1.5 (19) Carnosine 0.1 (20) Cyclomethicone, Dimethicone Crosspolymer 2.0 (21) Arbutin 0.5 (22) Polysorbate-20 2.0 (23) Ethyl Lactate 12.0. Procedure. Mix (1) to (13) and heat at 70 to 80 C till homogenous. Cool to 40 to 50 C. Premix (14) to (16) and add to batch with mixing. Mix (17) to (23) to a clear solution and add to main batch mix. Cool to room temperature. An off-white cream is obtained.

Example 11

Acne Cream

Ingredients. (1) Water 54.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Niacinamide Hydroxycitrate 2.2 (15) Ethyl Lactate 15.0 (16) Niacinamide Salicylate 4.0 (17) L-Proline Benfotiamine (from Example 2) 0.1 (18) Paeonol 1.5 (19) L-Proline-D-glucose-6-phosphate 0.1 (20) Cyclomethicone, Dimethicone Crosspolymer 2.0 (21) Arbutin 0.5 (22) Salicylic Acid 2.0 (23) Polysorbate-20 2.0 (24) Polyacrylamide 2.0. Procedure. Mix (1) to (15) and heat at 70 to 80 C till homogenous. Cool to 40 to 50 C. Premix (16) to (23) and heat, if necessary, to a solution and add to main batch with mixing. Cool to room temperature and add (24) and mix. An off-white cream is obtained.

Example 12

Skin Brightening Cleanser

Ingredients. (1) PEG-6 48.0 (2) Hydroxypropyl Guar 0.4 (3) Sodium Cocoyl Isethionate 20.0 (4) Sodium Lauryl Sulfoacetate 5.0 (5) *Boswellia Serrata* 0.05 (6) L-Glutathione 0.01 (7) Resveratrol 0.01 (8) L-Proline Benfotiamine (from Example 2) 0.1 (9) Glutathione-D-glucose-6-phosphate 0.3 (10) Ascorbic acid 10.0 (11) Phenoxyethanol 0.7 (12) Ethylhexylglycerin 0.3 (13) Fragrance 0.2 (14) Ethylhexyl Lactate 15.0. Procedure. Mix (1) and (2) to a clear thin gel. Add (3) and (4) and mix. Premix (5) to (14) to a solution. Add to main batch and mix. A white cream-like cleanser is obtained.

Example 13

Anti-Inflammatory Transparent Gel

Ingredients. (1) Ethyl Lactate 96.75 (2) Hydroxypropyl Guar 1.0 (3) L-Proline-Trehalose Phosphate Complex 0.1 (4) Capsaicin 0.25 (5) Magnolol (and) Honokiol 0.2 (6) Paeonol 0.5 (7) L-Proline ATP Disodium Complex 0.2 (8) Fragrance 1.0. Procedure. Mix (1) and (2) and heat at 50 to 60 C till clear. Cool to 40 to 45 C and add all other ingredients and mix. Cool to room temperature. A transparent gel-like product is obtained.

Example 14

Skin Darkening Clear Gel

Ingredients (1) Deionized water 79.0 (2) Preservative 0.7 (3) Ammonium Acryloyldimethyltaurate/VP Copolymer 2.0 (4) Glycerin 15.0 (5) Copper Glutathionate 0.1 (6) L-Tyrosine-D-glucose-6-phosphate 0.2 (7) Polysorbate-20 2.0 (8) Mucuna prurience extract 1.0. Procedure. Mix (1) to (4) till a clear gel is formed. Heat at 40 to 50 C and add all other ingredients with mixing. Cool to room temperature. Adjust pH to 3.5-4.0.

Example 15

Skin Darkening Cream in Combination with Dihydroxyacetone (DHA)

Ingredients (1) Deionized water 77.0 (2) Cetearyl alcohol (and) Dicetyl phosphate (and) Ceteth-10 phosphate 5.0 (3) Cetyl alcohol 2.0 (4) Glyceryl stearate (and) PEG-100 stearate 4.0 (5) Caprylic/capric triglyceride 5.0 (6) Mucuna prurience extract 1.0 (7) L-Tyrosine-D-glucose-6-phosphate 0.5 (8) Preservatives 0.5. (9) Dihydroxyacetone (DHA) 5.0. Procedure. Mix 1 to 5 and heat to 75-80° C. Adjust pH to 3.5-4.5. Cool to 35-40° C. with mixing. Add 6 to 9 with mixing. Adjust pH to 3.5-6.0. Off-white cream.

Example 16

A Method for the Topical Delivery

A method of topical delivery for cellular energy support comprising mixing of, (i) a mitoprotectant compound of FIG. 1, and (ii) an antioxidant agent, and (iii) an anti-inflammatory agent, and (iv) a collagen-boosting agent with a carrier, and wherein said mixture is applied to skin.

Practical Applications in Skin Care.

When an organic compound contains at least one carbon atom (asymmetric carbon) to which those four atoms attached are different in chemical nature, then that molecule is called chiral. The chiral molecules are left-handed or right-handed, depending on the orientation of those four atoms attached to the asymmetric carbon. Among popular methods of their nomenclature, chiral molecules are designated D or L; chiral atoms are labeled R or S. Chiral molecules have a unique physical property of deflecting a beam of polarized light to either left or right side of a centerline. However, a left-handed molecule, for example, may deflect polarized light to either left or right side of that centerline. The direction of that rotation is not directly related to either left- or right-handedness of a chiral molecule. The direction of light deflection is designated (+) for right-handed (d) and (−) for left-handed (l) rotation. The left-handed (L or S) and right-handed (D or R) molecules usually have different physical, chemical, and biological properties. Pharmaceuticals industry has utilized this variance in biological properties of chiral ingredients, both natural and synthetic, in the treatment of human ailments for a long time. Amoxicillin, a commonly prescribed penicillin derivative, has the chemical name (2S,5R,6R)-6-[(R)-(−)-2-amino-2-(p-hydroxyphenyl)acetamido]-3,3-dimethyl-7-oxo-4-thia-1-azabicyclo[3.2.0]heptane-2-carboxylic acid. In this case, the change of orientation of any of the carbons labeled S or R usually leads to the total loss of the biological activity. A large number of other pharmaceutical examples are known.

Chiral molecules exist everywhere. Human DNA is chiral, as are human body hormones, enzymes, and structural components of tissue, blood, hair, and skin. Amino acids are thought to be the first organic molecules produced on Earth via abiogenesis (Primordial Soup theory). All amino acids are chiral, with the exception of one. The applications of chiral ingredients in skin care and other topical products are abundant, popular examples of which are noted below.

Chirality in Ascorbic Acid. Ascorbic acid is a sugar acid possessing two chiral carbon atoms. The L-form of ascorbic acid is commonly known as vitamin C. A recent study has shown that D- and L-forms of ascorbic acid have different affinity for the enzyme tyrosinase. This would indicate that the skin whitening efficacy of L-ascorbic acid and D-ascorbic acid are vastly different. The efficacy of protective effects of D- and L-ascorbic acid on light-induced retinal damage in rats in another study showed greatly differect biological efficacy of these isomers. 5-Lipoxigenase, an enzyme causing cellular oxidative damage, is selectively inhibited by L-ascorbic acid; D-Ascorbic acid reverses this beneficial effect.

Chirality in α-Tocopherol (Vitamin E). α-Tocopherol is a chiral molecule. There are eight isomers of alpha-tocopherol that differ in the arrangement of groups around those chiran centers. Natural alpha-tocopherol is the "D-alpha" form. The synthetic form ("DL-alpha") is not as active as the natural tocopherol form. This is because natural "D-form" is recognized by the alpha-tocopherol transport protein, and thus maintained in the plasma, where the other non-natural isomers are not. Thus, the synthetic DL-α-tocopherol probably has only about half the vitamin activity of natural D-tocopherol in humans.

Chirality in Lipoic Acid. The carbon atom at C6 in lipoic acid is chiral and the molecule exists as two enantiomers R-(+)-lipoic acid (R-LA) and S-(−)-lipoic acid (S-LA) and as a racemic, 50/50 mixture R/S-lipoic acid (R/S-LA). R-lipoic acid, S-lipoic acid, and R/S-lipoic acid are pharmacologically distinct. Only the R-enantiomer (R-LA) of lipoic acid occurs naturally. Theoretically the S-isomer (S-LA) can assist in the reduction of the R-LA when a racemic (50% R and 50% S isomers) mixture is given but this is of questionable relevance in vivo. Several studies have demonstrated that S-LA either has lower activity than R-LA or interferes with the specific effects of R-LA by competitive inhibition. Lipoic acid has been found to increase the production of glutathione, responsible for glucose uptake in cells, R-LA has been shown to do so by a greater amount than either the S-LA or R/S-LA. This indicates that the specific effects of R-LA may be inhibited when S-LA is present.

Chirality in Amino Acids. Of 23 α-amino acids important in human biology, all but one (glycine) are chiral. These amino acids play a vital role in natural skin care; the production of skin and hair protective colorant (melanin), urocanic acid (sunscreen), cellular turnover, and protein synthesis are some of the examples. L-Tyrosine and L-dopa are used in hair darkening formulations. The inhibition of L-tyrosine and L-dopa synthesis (tyrosinase inhibitors) is used for skin whitening applications. L-Proline is a typical constituent of Osmoprotective skin care products.

Chiral molecules can undergo a process called racemization under certain conditions resulting in the formation of D and L mixtures. Formulating skin care products requires a combination of appropriate chiral ingredient and an effective delivery system that ensures optimal benefits. The topical delivery of chiral compounds in cosmetic and skin care compositions with their enhanced skin penetration and efficacy has not been disclosed in the prior art.

The formulas of the compounds of the present invention clearly indicate that skin care benefits of the two compounds that are combined are enhanced due to better skin penetration of the complexes of the present invention. L-Proline-benfotiamine, for example, provides the benefits of both L-proline and benfotiamine at an efficacy level higher than the use of L-proline and benfotiamine in an unreacted form. L-Tyrosine-D-glucose-6-phosphate provides better skin darkening due to enhanced melanin formation than L-tyrosine alone. The skin care benefits of certain compounds of the present invention are summarized in Table 3. Those benefits are based on the enhanced skin penetration of individual agents used in the preparation of said compounds, as noted in Table 3.

TABLE 3

| SKIN CARE BENEFITS. | | |
|---|---|---|
| COMPOUND | LITERATURE BENEFITS | ENHANCED BENEFITS |
| L-Proline | Collagen synthesis Protein folding Stem cell differentiation Protect again oxidation Osmoprotectant Stress protective | |
| Benfotiamine | Anti-glycation Anti-inflammation MMP inhibitor | |
| L-Carnosine | Collagen synthesis Cellular antioxidant Anti-glycation Cell repair Metal chelation | |
| Glutathione | Melanin synthesis inhibitor Intracellular antioxidant Mitochondria function DNA synthesis and repair Protein synthesis Prostaglandin synthesis Amino acid transport Enzyme activation | |
| L-Tyrosine | Melanin synthesis Protection of skin from sun Precursor of hormones | |

TABLE 3-continued

| SKIN CARE BENEFITS. | | |
|---|---|---|
| COMPOUND | LITERATURE BENEFITS | ENHANCED BENEFITS |
| D-Glucose-6-phosphate | Cell to cell communication | |
| Glutathione-D-glucose-6-phosphate | | Skin whitening Skin brightening Skin wrinkles and fine lines reduction Collagen synthesis |
| Adenosine-5'-triphosphate | Transports energy for metabolism | |
| Trehalose (Trehalose phosphate) | Stress protectant Protein folding protection | |
| L-Proline-L-Carnosine | | Collagen synthesis Cellular antioxidant Osmoprotectant Skin soothing Anti-glycation Skin detoxification Cell repair |
| L-Proline-benfotiamine | | Collagen synthesis Antioxidant Osmoprotectant Stress protective Anti-glycation Anti-inflammatory MMP inhibitor Appearance of aged skin Anti-lipoxidation products |
| L-Tyrosine-D-glucose-6-phosphate | | Skin tanning Protection of skin from sun |
| L-Tyrosine-ATP Disodium | | Skin tanning Protection of skin from sun |

Skin Darkening

Figure 2:
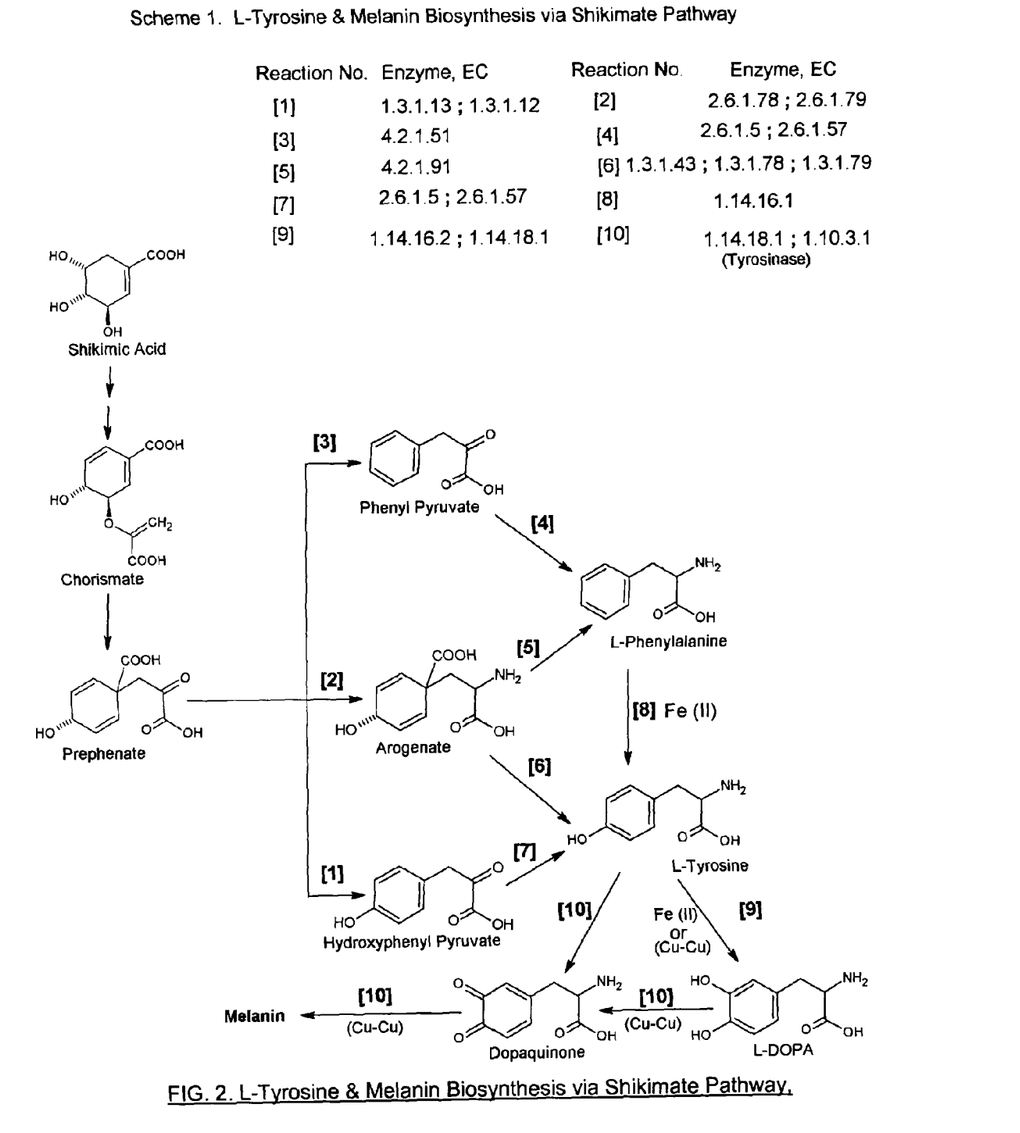
FIG. 2. Scheme 1. L-Tyrosine and Melanin Biosynthesis via Shikimate Pathway.

The present invention discloses compositions that activate body's own mechanism of skin darkening effect. This is achieved by the enhancement of the activity of tyrosinase enzyme with concurrent supply of the key substrates required for melanin synthesis by tyrosinase enzyme. L-Tyrosine, L-DOPA, and L-glutathione play a major role in the formation of melanin via the action of tyrosinase enzyme. This is further illustrated in FIG. 2. This biochemistry also requires transport of Cu to the active-site of tyrosinase. This transport requires energy provided by adenosine-5'-triphosphate (ATP). L-Tyrosine-disodium ATP and L-tyrosine-D-glucose-6-phosphate complexes, either alone or in combination, provide surprisingly enhanced skin tanning via their topical application.

Skin Whitening.

Glutathione has recently been used as an inhibitor of melanin in the cosmetics industry. In countries like the Philippines, this product is sold as a whitening soap. Glutathione competitively inhibits melanin synthesis in the reaction of tyrosinase and L-3,4-dihydroxyphenylalanine (L-DOPA) by interrupting L-DOPA's ability to bind to tyrosinase during melanin synthesis. The inhibition of melanin synthesis was reversed by increasing the concentration of L-DOPA, but not by increasing tyrosinase. Although the synthesized melanin was aggregated within 1 h, the aggregation was inhibited by the addition of glutathione. These results indicate that glutathione inhibits the synthesis and agglutination of melanin by interrupting the function of L-DOPA. Glutathione-D-glucose-6-phosphate shows enhanced skin penetration, thus providing superior skin whitening affects than glutathione;

Wrinkles and Fine Lines Reduction

L-Carnosine-D-glucose-6-phosphate undergoes faster skin penetration, thus providing enhanced collagen synthesis and intra-cellular anti-inflammatory activity resulting in reduced skin wrinkles and fine lines.

Challenged Skin Conditions.

Skin challenged by internal organ diseases and their various treatments causes skin condition that is common to diseases such as cancer and diabetes. This is further illustrated in FIG. 3.

Skin Penetration Data.

The skin penetration were determined by Franz diffusion cell method. For example, the results for L-Proline Benfotiamine are summarized in Table 3. These data clearly establish enhanced skin penetration of the agents of the present invention.

TABLE 3

SKIN PENETRATION DATA. FRANZ DIFFUSION CELL.

| Sample | Composition, gm | Relative Skin Penetration |
|---|---|---|
| L-Proline Benfotiamine (A) | Benfotiamine 1.0 L-Proline 4.0 Water 150.0 | A > C >> B |
| Benfotiamine (B) | Benfotiamine 1.0 Water 154.0 | |
| L-Proline (C) | L-Proline 4.0 Water 151.0 | |

The invention claimed is:

1. A complex of an L-amino acid derivative and a heterocyclic compound for topical application; wherein, said L-amino acid derivative is selected from the group consisting of an L-amino acid, L-amino ester, L-peptide, and hydrolyzed proteins, and, wherein, said complex is selected from the group consisting of:

-continued

-continued

-continued wherein,

R is an organic agent selected from the group consisting of,

-continued wherein;

R¹ is selected from the group consisting of H, and $C^1$-$C^{20}$ alkyl esters.

2. The complex of claim 1, wherein said compound is L-proline-benfotiamine, the chemical name of which is L-Proline-S-[(2Z)-2-{[(4-amino-2-methylpyrimidin-5-yl) methyl](formyl)amino}-5-(phosphonooxy)pent-2-en-3-yl] benzenecarbothioate (1:1), of formula), 3. The complex of claim 1, wherein said complex is Glutathione-D-glucose-6-phosphate, the chemical name of which is glutathione-D-glucopyranose 6-phosphate (1:1) or γ-L-Glutamyl-L-cysteinylglycine-D-glucopyranose 6-phosphate (1:1), of formula (), 4. The complex of claim 1, wherein said compound is β-Alanyl-L-histidine-D-glucose-6-phosphate, the chemical name of which is L-carnosine-D-glucopyranose 6-phosphate (1:1), of formula (),

5. A composition comprising the compound of claim 1 and a carrier for topical application.

6. A composition comprising the compound of claim 1 and a carrier to treat a dermatological disorder selected from the group consisting of sun-burn; age spots, acne, skin wrinkles including fine lines, dry skin, liver spots, pigmented spots, dark circles under the eyes, skin pigmentation including darkened skin, blemishes, oily skin, inflammation, and combinations thereof.

7. A composition of claim 6, wherein said dermatological disorder is sun-burn.

8. A method of treating a dermatological disorder selected from the group consisting of sunburn, age spots, acne, wrinkles, fine lines, dry skin, liver spots, pigmentation spots, dark circles under the eyes, skin pigmentation, blemishes, oily skin, inflammation, or combinations thereof comprising mixing of, (i) a mitoprotectant compound of claim 1, and (ii) an antioxidant agent, and (iii) an anti-inflammatory agent, and (iv) a collagen-boosting agent with a carrier, and wherein said mixture is applied to skin.

9. The method of claim 8, wherein said mitoprotectant complex is L-carnosine-D-glucose-6-phosphate of formula, 10. The method of claim 8, wherein antioxidant agent is hypericin.

11. The method of claim 8, wherein anti-inflammatory agent is baicalein.

12. The method of claim 8, wherein collagen-boosting agent is L-ergothioneine.

13. The method of claim 8 for the treatment of dermatological disorder selected from the group consisting of sun-burn, age spots, acne, skin wrinkles including fine lines, dry skin, liver spots, pigmented spots, dark circles under the eyes, skin pigmentation including darkened skin, blemishes, oily skin, inflammation, and combinations thereof.

14. The method of claim 13, wherein said dermatological disorder is skin wrinkles including fine lines.

15. A process for making compound of claim 1, which comprises combining; (i) An organic phosphorylated agent, and
    (ii) An L-amino acid derivative, and
    (iii) A liquid reaction medium, and
    (iv) Heating at 50 to 120 degrees Celsius.

16. The process of claim 15, wherein said organic phosphorylated agent is D-glucose-6-phosphate.

17. The process of claim 15, wherein said L-amino acid derivative is L-Carnosine.

18. The process of claim 15, wherein said liquid reaction medium is selected from the group comprising water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methylpyrrolidone, pyrrolidone, and combinations thereof.

19. The process of claim 18, wherein said liquid reaction medium is water.

* * * * *